United States Patent [19]

Diot et al.

[11] Patent Number: 4,992,264

[45] Date of Patent: Feb. 12, 1991

[54] **NOVEL COSMETIC COMPOSITIONS CONTAINING AN EXTRACT OF THE AERIAL PARTS OF *CICHORIUM INTYBUS* L**

[76] Inventors: Michel Diot, 2 allée des Dimanches, Louveciennes, France, 78430; Claude Bonne, 316 avenue d'Occitanie, Montpellier, France, 34000

[21] Appl. No.: 411,471

[22] PCT Filed: Jan. 27, 1989

[86] PCT No.: PCT/EP89/00073

§ 371 Date: Sep. 27, 1989

§ 102(e) Date: Sep. 27, 1989

[87] PCT Pub. No.: WO89/06954

PCT Pub. Date: Aug. 10, 1989

[30] Foreign Application Priority Data

Jan. 29, 1988 [FR] France .................. 88 01464

[51] Int. Cl.$^5$ .................. A61K 7/48; A61K 35/78
[52] U.S. Cl. .................. 424/63; 424/195.1; 514/783
[58] Field of Search .................. 424/195.1, 63, 69; 514/783, 937, 938

[56] References Cited

FOREIGN PATENT DOCUMENTS 2596986 10/1987 France .
2597337 10/1987 France .
 550002  4/1974 Switzerland .

OTHER PUBLICATIONS

Hagers Handbuch der Pharmazeutischen Praxis, vol. 4, edition 4, 1973, pp. 4–5, Springer-Verlag, Berlin, DE; p. 4, "*Cichorium intybus*"–p. 5.

G. Garnier et al.: "Ressources Medicinales de la Flore Francaise", Tome II, 1961, pp. 1448–1451, Vigot Frères Editeures, Paris, FR; p. 1450, Pharmacologie.

*Primary Examiner*—Merrell C. Cashion, Jr.
*Assistant Examiner*—Susan S. Rucker
*Attorney, Agent, or Firm*—Wegner, Cantor, Mueller & Player

[57] ABSTRACT

The subject of the invention is a cosmetic composition which prevents ageing of the skin, wherein the active ingredient is an extract of the aerial parts of *Cichorium intybus* L and the efficacy of which resides in its capacity to inhibit radical reactions, in particular by the chelation of iron.

6 Claims, No Drawings

NOVEL COSMETIC COMPOSITIONS CONTAINING AN EXTRACT OF THE AERIAL PARTS OF *CICHORIUM INTYBUS* L

The present invention relates to a cosmetic composition which prevents ageing of the skin. The present invention relates more particularly to a cosmetic composition containing an extract of the aerial parts of *Cichorium intybus* L. as active ingredient.

The extract of *Cichorium intybus* L. (compounds) contains various polyphenolic derivatives such as caffeyltartaric acid.

The extrace of *Cichorium intybus* L. can be prepared by extraction of the dried aerial parts with the aid of polar solvents such as boiling water, methanol, ethanol and propylene glycol.

The leaves of this plant are known for their choleretic, diuretic and mildlylaxastive properties which are the reason for infusions of it being used as a depurant in folk medicine.

The applicants have in fact discovered that an extract of the aerial parts of *Cichorium intybus* L. has an anti-radical activity, in particular as a result of complexing rion, and that cosmetic compositions containing such an extract can prevent the harmful effects of the free radicals which are, in part, responsible for cutaneous ageing.

The free radicals are produced during the course of the reactions of cell metabolism, in particular as a result of the one-electron reduction of oxygen during the reactions of mitochondrial respiration.

They are also produced in the skin by photochemical reactions during exposure to the sun. There exists a powerful system of protection against such radicals in an intact cell. The superoxide anion ($O_2.-$) is converted by the superoxide dismutases to hydrogen peroxide ($H_2O_2$) which is, in turn, metabolized to water ($H_2O$) by catalase. The superoxide dismulase±catalase couple is a detoxification system whose efficacy decreases during ageing. Under these conditions, $O_2.-$ and $H_2O_2$ react to generate a cascade of reactions, catalyzed by iron and known as the HABER-WEISS reaction, and which lead in particular to the formation of the hydroxyl (OH·) radical. This radical exhibits a very high reactivity and interacts with biological structures, in particular the membrane phospholipids, proteins and nucleic acids, to which it causes damage.

It is known that neither the superoxide anion nor hydrogen peroxide can induce the peroxidation of lipids or a sugar such as deoxyribose directly.

In fact, this reaction requires the formation of more reactive radicals such as the hydroxyl radical OH·, which is catalyzed by iron.

When such radicals attack the fatty acids of the membrane phospholipids, a disorganization spreads through the cell membranes, inhibiting their functions and, especially in regard to the epidermis, their role as barrier which ensures adequate cutaneous hydration. Similarly, when these radicals interact with the proteins of the skin such as elastic and collagen, they bring about rupture and cross-linking characteristic of cutaneous ageing.

As a consequence of the presence of the extract of the aerial parts of *Cichorium intybus* L. which inhibits these free radicals, notably by chelating iron, the cosmetic composition according to the present invention is able to prevent ageing of the skin.

The cosmetic composition according to the present invention advantageously contains the extract of the aerial parts of *Cichorium intybus* L. at a concentration expressed in polyphenol content of from 0.001 to 0.01% by weight.

Another subject of the present invention is a process for the prevention of ageing of the skin, wherein at least one extract of the aerial parted of Cichorium intybus L. is applied to the skin in a suitable cosmetic base.

The extract may be prepared in the following manner.

EXAMPLE OF THE PREPARATION OF THE EXTRACT

The aerial parts of Cichorium intybus L. are dried and chopped up without actually being ground to a power). They are extracted with 5 times their weight of boiling water (maceration for 30 minutes). The extract is filtered, then the residue is extracted with propylene glycol (5times the initial weight of plant). The propylene glycol extract is filtered, the residue is dried with the aid of a press and the extracts are pooled.

The water/propylene glycol extract (50:50) contains 1±0.2 mg/ml of polyphenols which include caffeyltartaric acid (measured by the ARNOW reagent).

The following experimental protocols enable the activity of the extract, the active ingredient used in the present invention, to be demonstrated.

INHIBITION OF THE FENTON REACTION

The Fenton reaction is the third step in the HABER-WEISS reaction.

(1) $O_2^- \pm Fe^{3\pm} \rightarrow Fe^{2\pm} \pm O_2$     (1)

(2) $2O_2^{·-} \pm 2H^{35} \rightarrow H_2O_2 \pm O_2$     (2)

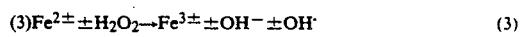

(3) $Fe^{2\pm} \pm H_2O_2 \rightarrow Fe^{3\pm} \pm OH^- \pm OH·$     (3)

This reaction is carried out in vitro by reacting $H_2O_2$ ($10^{-4}M$)±$Fe^{2\pm}$($10^{-5}M$) in the presence of hypoxanthine and xanthine oxidase, which generates the superoxide anion, and deoxyribose ($5 \times 10^{313}M$), the substrate of the peroxidation reaction.

When the reaction is carried out in the presence of EDTA (ethylenediamine tetraacetic acid), the radical generated is OH· according to the reaction described above. In contrast, in the absence of EDTA another, still unknown type of radical is generated (WINTERBOURN, C.C. Free Radical Biology & Medicine, 3, 33–39, 1987).

In the absence or the presence of EDTA, the reaction converts doxyribose into oxidation products which can be measured by thiobarbituric acid according to the method described by GUTTERIDGE, J.M.C. (Biochem. J., 224, 761–767, 1984)

The active ingredients of the extract of Cichorium intybuys L. inhibit the oxidation of deoxyribose when added to the reaction mixtures under the two sets of conditions:

| Active ingredients of Cichorium intybus (ug/ml) | EDTA ($5 \times 10^{-5}M$) | Inhibition of the oxydation of deoxyribose % |
|---|---|---|
| 10 | + | 41 |
| 10 | − | 15 |

-continued

| Active ingredients of Cichorium intybus (ug/ml) | EDTA ($5 \times 10^{-5}$M) | Inhibition of the oxydation of deoxyribose % |
| --- | --- | --- |
| 50 | + | 62 |
| 50 | − | 30 |
| 100 | + | 75 |
| 100 | − | 49 |

INHIBITION OF THE FORMATION OF CUTANEOUS MALONALDEHYDE

One of the signs of cellular ageing which implicates free radicals in the ageing process if the accumulation of lipofuscins in the tissues. These pigments are Schiff bases resulting from the reaction of primary amines with the malonaldehyde (MDA) produced by radical destruction of lipids and certains sugars.

The protective effect of the extract against this process can be demonstrated in a test in which, when diluted in a cosmetic excipient and applied to the skin of a laboratory animal, the extract inhibits the formation of MDA normally induced by irradiation of the cutaneous tissue. A typical experiment is given below:

Nude mice where sensitized by being bathed for 5 minutes in a solution of Rose bengal ($10^{-5}$M), then dried in the dark. The diluted extract of the excipient was applied to the surface of the dorsal skin of the animals 10 minutes before they were irradiated. Irradiation was carried out for 30 minutes with the aid of a 75 watts KRYPTON incandescent lamp placed at a distance of 25 cm from the animals. Control mice were kept in the dark. The animals were sacrificed and samples of their epidermis were taken for analysis of MDA by means of the thiobarbituric acid reaction referred to above. The results are reported below and demonstrate the protective effect of the extract against cutaneous damage due to peroxidation triggered by a photochemical reaction.

| TREATMENT | MDA (% variation) |
| --- | --- |
| controls irradiated | +120% |
| excipient irradiated 5% extract* | −40% |

*extract containing 1 mg of polyphenols/ml.

The cosmetic compositions according to the invention may in addition contain, if desired, any other substance known to have beneficial properties in beauty care, such as collagen, elastin, hyaluronic acid, lipid compounds containing unsaturated fatrty acids, liposomes, phospholipids, humectants, vitamin extracts, perfumes, preservatives, coloring matters. They may also contain sun filters.

The cosmetic compositions according to the invention are available in all of the forms used in beauty care, such as creams or gels in jars or tubes, milks, lotions in glass or plastic bottles and, if required, dispensing vials or even ampoules or sprays.

For each preparation recourse is had to appropriate excipients. These excipients must have all of the properties usually required. Examples which may be cited are: glycerol stearate, propylene glycol, lanolin, glycerol, cetyl alcohol, polyols, vegetable, animals and mineral oils, phospholipids such as liposomes, the waxes, wetting agents, binding, stabilizing and emulsifying agents commonly used.

The different cosmetic forms mentioned above are prepared according to the methods used in this field.

Below are given examples of cosmetic compositions (in parts by weight) prepared by using an extract of Cichorium intybus L. containing 1 mg/ml of polyphenols.

| 1. O/W Cream | |
| --- | --- |
| Wheat germ oil | 10 |
| Cichorium intybus extract | from 2 to 10 |
| Propylene glycol | 5 |
| Carboxyvinyl polymer | 0.5 |
| Triethanolamine | 0.5 |
| Aromatic composition | q.s. |
| preservatives | q.s. |
| Water | up to 100 |
| 2. W/O Cream | |
| Cetyl alcohol | 0.5 |
| Anhydrous lanolin | 0.5 |
| Wheat germ oil | 1 |
| Polyethoxyetherphosphate of oleyl alcohol | 1.5 |
| Triethanolamine | 0.5 |
| Cichorium intybus extract | from 2 to 10 |
| Magnesium aluminum silicate | 0.5 |
| Aromatic composition | q.s. |
| Preservatives | q.s. |
| Water | up to 100 |
| 3. Aqueous-alcoholic lotion | |
| Stearic acid | 5 |
| Glycerol | 3 |
| Cichorium intybus extract | from 2 to 10 |
| Na alginate | 0.2 |
| Thiethanolamine | 0.5 |
| 95° Alcohol | 5 |
| Water | up to 100 |

We claim:

1. Cosmetic composition preventing aging of the skin, containing an extract of the aerial parts of Cichorium intybus L. at a concentration expressed in polyphenols of from 0.001 to 0.01% by weight, in an appropriate cosmetic base.

2. Composition according to claim 1, wherein the extract is an extract by a polar solvent of the aerial parts of Cichorium intybus L.

3. Process for the preparation of a composition according to claim 1, wherein an extract of the aerial parts of Cichorium intybus L., at a concentration expressed in polyphenols of from 0.001 to 0.01% of the weight, is mixed with an appropriate cosmetic base.

4. Process as claimed in claim 3, wherein the extract is an extract by a polar solvent of the aerial parts of Cichorium intybus L.

5. Process for preventing aging of the skin, wherein an extract of the aerial parts of Cichorium intybus L., at a concentration expressed in polyphenols of from 0.001 to 0.01 by weight, is applied to the skin in an appropriate cosmetic base.

6. Process according to claim 5, wherein the extract is an extract by a polar solvent of the aerial parts of Cichorium intybus L.

* * * * *